United States Patent [19]

Fuchs et al.

[11] 4,317,834
[45] Mar. 2, 1982

[54] COMBATING ARTHROPODS WITH FLUORINE-SUBSTITUTED SPIRO-CARBOXYLIC ACID BENZYL ESTERS

[75] Inventors: Rainer Fuchs, Wuppertal; Klaus Naumann, Leverkusen; Ingeborg Hammann, Cologne; Bernhard Homeyer, Leverkusen; Wolfgang Behrenz, Overath; Wilhelm Stendel, Wuppertal, all of Fed. Rep. of Germany

[73] Assignee: Bayer Aktiengesellschaft, Leverkusen, Fed. Rep. of Germany

[21] Appl. No.: 203,032

[22] Filed: Nov. 3, 1980

[30] Foreign Application Priority Data

Nov. 23, 1979 [DE] Fed. Rep. of Germany ....... 2947209

[51] Int. Cl.³ .................... A01N 53/00; C07C 69/753; C07C 121/75
[52] U.S. Cl. ............................ 424/304; 260/465 D; 424/305; 424/308; 560/8; 560/117; 560/118
[58] Field of Search ......................... 560/8, 117, 118; 260/465 D; 424/304, 308, 305

[56] References Cited

U.S. PATENT DOCUMENTS 3,962,458 6/1976 Schrider ............................ 424/304
3,966,959 6/1976 Addor ................................ 424/304

FOREIGN PATENT DOCUMENTS 846544 3/1977 Belgium .
2621433 12/1977 Fed. Rep. of Germany .

Primary Examiner—Dolph H. Torrence
Attorney, Agent, or Firm—Sprung, Felfe, Horn, Lynch & Kramer

[57] ABSTRACT

Fluorine-substituted spirocarboxylic acid benzyl esters of the formula

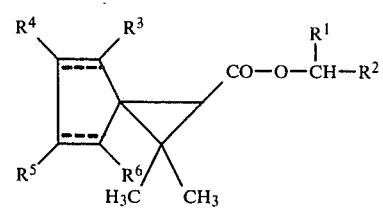

in which $R^1$ represents hydrogen, cyano or alkyl, alkenyl or alkynyl, with in each case up to 4 carbon atoms, $R^2$ represents a phenyl radical which is substituted by halogen and/or by optionally halogen-substituted phenoxy, with the proviso that the radical $R^2$ contains in total at least one fluorine substituent, and $R^3$, $R^4$, $R^5$ and $R^6$ each represent hydrogen, halogen or alkyl, or $R^3$ and $R^4$, taken together, and/or $R^5$ and $R^6$, taken together, represent alkanediyl (alkylene) or a fused-on benzo radical, and the C atoms of the 5-member spirocyclic ring are linked to one another either by double bonds or by single bonds, which possess arthropodicidal properties.

8 Claims, No Drawings

COMBATING ARTHROPODS WITH FLUORINE-SUBSTITUTED SPIRO-CARBOXYLIC ACID BENZYL ESTERS

The invention relates to certain new fluorine-substituted spirocarboxylic acid benzyl esters, to a process for their preparation and to their use as agents for combating pests, especially as arthropodicides and in particular as insecticides and acaricides.

It is known that certain cyclopropanecarboxylic acid esters, for example 3-(2-methyl-prop-1-ene-1-yl)-2,2-dimethyl-cyclopropane-1-carboxylic acid 3-phenoxybenzyl ester and 3,3-dimethylspiro-(cyclopropane-1,1'-indene)-2-carboxylic acid 3-phenoxybenzyl ester, have insecticidal and acaricidal properties (see U.S. Pat. No. 3,962,458 and British Patent Specification No. 1,234,858). However, the action of these compounds is not always satisfactory, especially in the case of low concentrations of active compound and when small amounts are applied.

The present invention now provides, as new compounds, the fluorine-substituted spirocarboxylic acid benzyl esters of the general formula

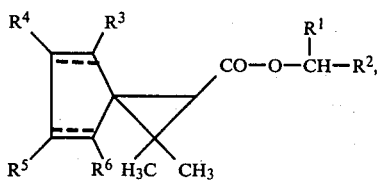

in which $R^1$ represents hydrogen, cyano or alkyl, alkenyl or alkynyl, with in each case up to 4 carbon atoms, $R^2$ represents a phenyl radical which is substituted by halogen and/or by optionally halogen-substituted phenoxy, with the proviso that the radical $R^2$ contains in total at least one fluorine substituent, and $R^3$, $R^4$, $R^5$ and $R^6$ each represent hydrogen, halogen or alkyl, or $R^3$ and $R^4$, taken together, and/or $R^5$ and $R^6$, taken together, represent alkanediyl (alkylene) or a fused-on benzo radical, and the C atoms of the 5-membered spirocyclic ring are linked to one another either by double bonds or by single bonds.

The general formula (I) also includes the various possible stereoisomers and optically active isomers and mixtures thereof.

Preferred compounds of the formula (I) are those in which $R^1$ represents hydrogen or cyano, $R^2$ represents pentafluorophenyl, 4-fluoro-3-phenoxyphenyl, 3-(4-fluoro-phenoxy)-phenyl or 4-fluoro-3-(4-fluoro-phenoxy)-phenyl, $R^3$ and $R^4$ represent hydrogen and $R^5$ and $R^6$ together represent a fused-on benzo radical, and at the same time the carbon atoms bonded to $R^3$ and $R^4$ and to $R^5$ and $R^6$ are linked to one another via double bonds.

The invention also provides a process for the preparation of a compound of the formula (I) in which a spirocarboxylic acid of the general formula

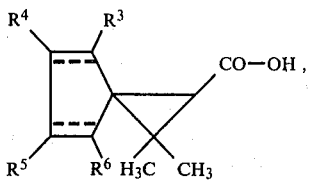

in which $R^3$, $R^4$, $R^5$ and $R^6$ have the meanings indicated above, or a reactive derivative thereof, is reacted with an alcohol of the general formula

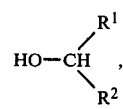

in which $R^1$ and $R^2$ have the meanings indicated above, or with a reactive derivative thereof, if appropriate in the presence of an acid acceptor and/or a catalyst and if appropriate using a diluent.

The fluorine-substituted spirocarboxylic acid benzyl esters of the formula (I) are distinguished by a high insecticidal and acaricidal activity.

Surprisingly, the compounds of the formula (I) exhibit a considerably more powerful insecticidal and acaricidal action than the compounds known from the state of the art which have an analogous structure and the same type of action.

In a preferred variant (a) of the process for the preparation of a compound of the formula (I), a spirocarboxylic acid chloride of the general formula

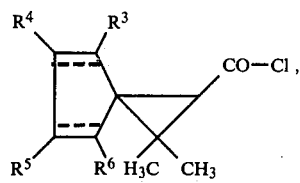

in which $R^3$, $R^4$, $R^5$ and $R^6$ have the meanings indicated above, is reacted with a benzyl alcohol of the formula (III) above in the presence of an acid acceptor and using a diluent.

In another preferred process variant (b), in particular for the preparation of a compound of the formula (I) in which $R^1$ represents cyano and $R^2$ represents fluorine-substituted phenoxy-phenyl, an acid chloride of the formula (IIa) above is reacted with a corresponding phenoxy-benzaldehyde of the general formula $$OCH-R^2 \qquad (IV),$$

in which $R^2$ represents fluorine-substituted phenoxy-phenyl, and at least an equimolar amount of an alkali metal cyanide (especially sodium cyanide or potassium cyanide) in the presence of water and a water-immiscible organic solvent, and if appropriate in the presence of a catalyst.

Other reactive derivatives of the carboxylic acids of the formula (II) which may be mentioned are lower (for example $C_1$–$C_4$) alkyl esters thereof, which can be reacted with alcohols of the formula (III) by customary methods.

Alkali metal salts, alkaline earth metal salts or ammonium salts of the carboxylic acids (II) can likewise be reacted with benzyl halides, which are derived from benzyl alcohols of the formula (III), to give compounds of the formula (I).

If, for example, 3,3-dimethyl-spiro-(cyclopropane-1,1'-indene)-2-carboxylic acid chloride and pentafluorobenzyl alcohol are used as starting substances in process variant (a) and 3,3-dimethylspiro-(cyclopropane-1,1'-indene)-2-carboxylic acid chloride and 4-fluoro-3-(4-fluoro-phenoxy)-benzaldehyde are used as starting substances in process variant (b), the respective reactions can be outlined by the following equations:

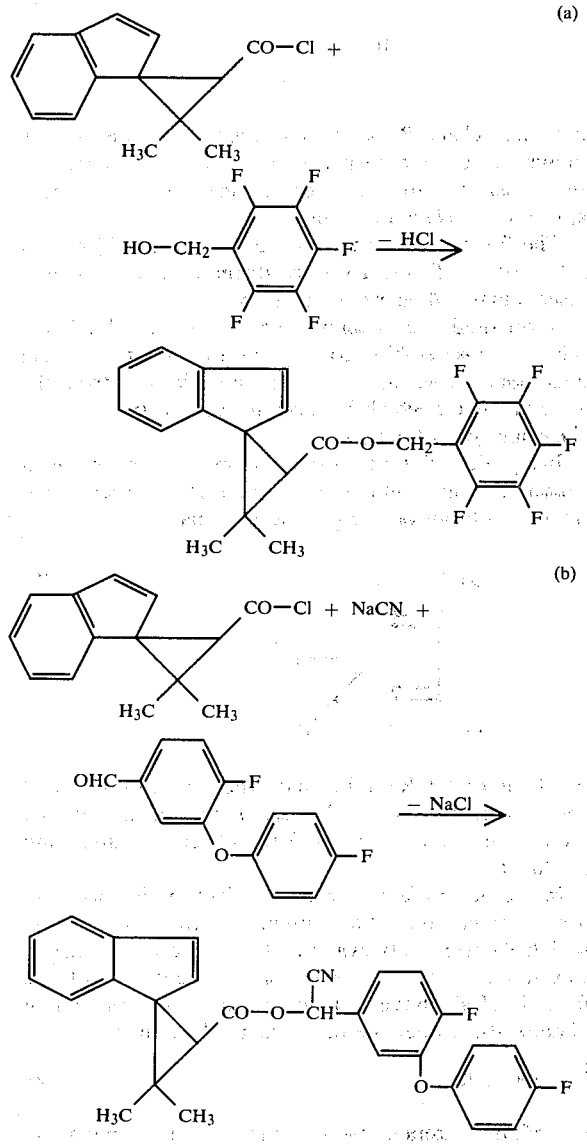

The spirocarboxylic acids of the formula (II) and corresponding acid chlorides of the formula (IIa) to be used as starting compounds are already known (see, for example, U.S. Pat. No. 3,962,458, DE-OS (German Published Specification) Nos. 2,727,909 and 2,713,651, Belgian Patent Specification Nos. 846,544 and 820,418 and Japanese Pat. No. 51/148,024).

Those acid chlorides of the formula (IIa) which have not hitherto been described in the literature can be prepared in the customary manner, for example by reacting the corresponding acid of the formula (II) with thionyl chloride, if appropriate in the presence of a diluent, for example carbon tetrachloride, at temperatures between 10° and 100° C.

Formula (III) provides a definition of the benzyl alcohols also to be used as starting substances. Preferably, in this formula, $R^1$ and $R^2$ represent those radicals which have already been mentioned as preferred in the case of the definition of the radicals $R^1$ and $R^2$ in formula (I).

Examples of the starting compounds of the formula (III) which may be mentioned are: pentafluorobenzyl alcohol, 4-fluoro-3-phenoxy-benzyl alcohol, 3-(4-fluoro-phenoxy)-benzyl alcohol, 4-fluoro-3-(4-fluoro-phenoxy)-benzyl alcohol and 3-(4-fluoro-phenoxy)-α-cyano-benzyl alcohol.

The starting compounds of the formula (III) are already known (see British Patent Specification No. 1,078,511 and DE-OS (German Published Specification) No. 2,621,433, U.S. application Ser. No. 877,536, filed Feb. 13, 1978, and U.S. Pat. No. 4199596 issued Apr. 22, 1980.

Formula (IV) provides a definition of the phenoxybenzaldehydes which can be used as starting substances. Preferably, in this formula, $R^2$ represents those radicals which have already been mentioned as preferred in the case of the definition of $R^2$ in formula (I). Examples which may be mentioned are: 4-fluoro-3-phenoxy-benzaldehyde, 3-(4-fluoro-phenoxy)-benzaldehyde and 4-fluoro-3-(4-fluoro-phenoxy)-benzaldehyde.

The phenoxybenzaldehydes of the formula (IV) are already known (see DE-OS (German Published Specification) No. 2,621,433, U.S. application Ser. No. 877,536 and U.S. Pat. No. 4,199,596).

All variants of the process for the preparation of the compounds of the formula (I) are preferably carried out using a diluent. Possible diluents are virtually any of the inert organic solvents. These include, as preferences, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene; ethers, such as diethyl ether, dibutyl ether, glycol dimethyl ether, diglycol dimethyl ether, tetrahydrofuran and dioxane; ketones, such as acetone, methyl ethyl ketone, methyl isopropyl ketone and methyl isobutyl ketone; esters, such as methyl acetate and ethyl acetate; nitriles, for example acetonitrile and propionitrile; amides, for example dimethylformamide, dimethylacetamide and N-methylpyrrolidone; and dimethylsulphoxide, tetramethylene sulphone and hexamethylphosphoric acid triamide.

Variant (a) of the process according to the invention is preferably carried out in the presence of an acid acceptor. Acid acceptors which can be used are any of the customary acid-binding agents. Acid-binding agents which have proved particularly suitable are alkali metal carbonates and alcoholates, such as sodium carbonate, potassium carbonate, sodium methylate and ethylate and potassium methylate and ethylate, and furthermore aliphatic, aromatic or heterocyclic amines, for example triethylamine, trimethylamine, dimethylaniline, dimethylbenzylamine, pyridine, diazabicyclooctane, diazabicyclononane and diazabicycloundecene.

Variant (b) of the process according to the invention is carried out in the presence of water and an organic solvent which is immiscible with water, generally one of those mentioned above. The above-mentioned hydrocarbons are particularly suitable for this variant.

Catalysts which are used in process variant (b) are preferably compounds which are suitable for the transfer of anions from water into organic solvents. Examples of these compounds are benzyl-triethyl-ammonium bisulphate, tetrabutylammonium bromide ad methyl-trioctyl-ammonium chloride (Aliquat 336).

The reaction temperature can be varied within a substantial range in all process variants. In general, the reaction is carried out between 0° and 100° C., preferably at from 10° to 50° C.

The process according to the invention is in general carried out under normal pressure. The starting substances are usually employed in equimolar amounts for carrying out the process according to the invention. An excess of one or the other of the reactants provides no significant advantages. The starting substances are brought together in a suitable diluent and the mixture is stirred until the reaction has ended, if appropriate after adding an acid acceptor and/or a catalyst.

Working up can be carried out by customary methods, for example by a procedure in which the reaction mixture is diluted, if appropriate, with water and/or a water-immiscible organic solvent, for example toluene, the organic phase is filtered off, washed with water, dried and filtered and the solvent is carefully distilled off from the filtrate under reduced pressure and at moderately elevated temperature ("incipient distillation").

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistic citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podona, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hyloptrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., Dermanyssus gallinae, Eriophyes ribis, Phyllocoptruta oleivora, Boophilus spp., Rhipicephalus spp., Ambylomma spp., Hyalomma spp., Ixodes spp., Psoroptes spp., Chorioptes spp., Sarcoptes spp., Tarsonemus spp., Bryobia praetiosa, Panonychus spp. and Tetranychus spp..

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.0001 to 1% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The active compounds according to the invention are used in a known manner in the veterinary sector, such as by dermal application, for example by means of dipping, spraying, pouring on and spotting on and dusting, and by parenteral administration, for example by means of an injection, as well as by oral administration via the feed or drinking water, for example in the form of tablets, capsules, powders, granules or drinks, and/or by the so-called feed trough method, for combating insects in the faeces of warm-blooded animals.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (especially arthropods and in particular insects or acarids) which comprises applying to the pests, or to a habitat thereof, a compound of the present invention alone or in the form of a composition containing as active ingredient a compound of the present invention in admixture with a diluent or carrier.

The present invention also provides a method of freeing or protecting domesticated animals from parasites which comprises applying to said animals a compound according to the present invention, in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasites by the application to said animals of a compound according to the present invention, in admixture with a diluent or carrier.

EXAMPLE 1

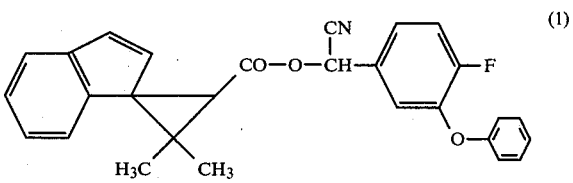

5 g (0.0232 mol) of 3-phenoxy-4-fluoro-benzaldehyde and 5.4 g (0.0232 mol) of 3,3-dimethylspiro-(cyclopropane-1,1'-indene)-2-carboxylic acid chloride were together added dropwise to a mixture of 1.8 g of sodium cyanide, 2.7 ml of water, 100 ml of n-hexane and 0.5 g of tetrabutylammonium bromide at 20°–25° C., while stirring, and the mixture was subsequently stirred at 20°–25° C. for 4 hours. 300 ml of toluene were then added to the reaction mixture and the mixture was extracted twice by shaking with 300 ml of water each time. The organic phase was separated off and dried over magnesium sulphate and the solvent was distilled off under a water-pump vacuum. Last residues of solvent were removed by brief incipient distillation at a bath temperature of 60° C./1 mm Hg. 8.1 g (79.5% of theory) of 3,3-dimethylspiro-(cyclopropane-1,1'-indene)2-carboxylic acid α-cyano-3-phenoxy-4-fluoro-benzyl ester were obtained as a viscous oil. The structure was confirmed by the $^1$H-NMR spectrum.

EXAMPLE 2

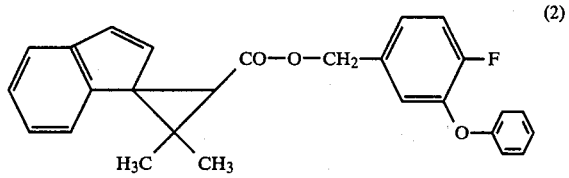

(2)

5.05 g (0.0232 mol) of 3-phenoxy-4-fluoro-benzyl alcohol and 5.4 g (0.0232 mol) of 3,3-dimethyl-spiro(cyclopropane-1,1'-indene)-2-carboxylic acid chloride were dissolved in 100 ml of anhydrous toluene, and 2.5 g of pyridine, dissolved in 50 ml of toluene, were added dropwise at 20°–25° C., while stirring. The mixture was stirred at 25°–35° C. for a further 3 hours. The reaction mixture was poured into 150 ml of water, to which 5 ml of concentrated hydrochloric acid were added, and the organic phase was separated off and washed again with 100 ml of water. The toluene phase was then dried over sodium sulphate and the solvent was distilled off under a waterpump vacuum. Last residues of solvent were removed by brief incipient distillation at a bath temperature of 60° C./1 mm Hg. 8.3 g (86.4% of theory) of 3,3-dimethylspiro-(cyclopropane-1,1'-indene)-2-carboxylic acid 3-phenoxy-4-fluoro-benzyl ester were obtained as a viscous oil. The structure was confirmed by the $^1$H-NMR spectrum.

The pesticidal activity of the compounds of this invention is illustrated by the following examples wherein the compounds according to the present invention are each identified by the number (given in brackets) from Examples 1 and 2 hereinabove.

EXAMPLE 3

Phaedon larvae test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (Brassica oleracea) were treated by being dipped into the preparation of the active compound and were infested with mustard beetle larvae (Phaedon cochleariae), as long as the leaves were still wet.

After the specified periods of time, the degree of destruction was determined in %: 100% meant that all of the beetle larvae had been killed whereas 0% meant that none of the beetle larvae had been killed.

In this test, for example, the following compound showed a superior activity compared with the prior art: (I).

EXAMPLE 4

Test insect: Phorbia antiqua grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compound showed a superior action compared with the prior art: (1).

EXAMPLE 5

Test insects: Sitophilus granarius
Number of test insects: 25
Solvent: Acetone

The active compound was taken up in the solvent at a rate of 2 g per liter. The solution so obtained was diluted with further solvent to the desired concentrations.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the test insects was observed 3 days after the commencement of the experiments. The destruction, in %, was determined. 100% denoted that all of the test insects had been killed; 0% denoted that none of the test insects had been killed.

In this test, for example, the following compounds showed a superior action compared with the prior art: (I) and (2).

EXAMPLE 6

LT₁₀₀ test for Diptera

Test Insects: *Musca domestica*, resistant
Number of test insects: 25
Solvent: Acetone The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. The stated number of test insects was then placed in the Petri dish and the dish was covered with a glass lid.

The condition of the test insects was continuously observed. The time which was necessary for 100% "knock down" was determined.

In this test, for example, the following compounds showed a superior action compared with the prior art: (I) and (2).

EXAMPLE 7

Test with *Lucilia cuprina* res. larvae

Solvent:
35 parts by weight of ethylene glycol monomethyl ether
35 parts by weight of nonylphenol polyglycol ether To produce a suitable preparation of active compound, three parts by weight of active compound were mixed with seven parts by weight of the above-mentioned solvent mixture and the concentrate thus obtained was diluted with water to the particular desired concentration.

About 20 *Lucilia cuprina* res. larvae were introduced into a test tube which contained approximately 1 cm³ of horse muscle and 0.5 ml of the preparation of active compound. After 24 hours, the degree of destruction was determined.

In this test, for example, the following compounds showed a superior action compared with the prior art: (1) and (2).

EXAMPLE 8

Test with *Musca autumnalis*

Solvent:
35 parts by weight of ethylene glycol monomethyl ether
35 parts by weight of nonylphenol polyglycol ether To produce a suitable preparation of active compound, three parts by weight of active compound were mixed with seven parts by weight of the above-mentioned solvent mixture and the concentrate thus obtained was diluted with water to the particular desired concentration.

10 *Musca autumnalis* adults were introduced into Petri dishes containing filter paper discs of appropriate size which had been saturated one day before the start of the experiment with 1 ml of the preparation of active compound to be tested. After 3 hours, the degree of destruction was determined.

In this test, for example, the following compound showed a superior action compared with the prior art: (1).

EXAMPLE 9

Test with *Boophilus microplus* resistant

Solvent:
35 parts by weight of ethylene glycol monomethyl ether
35 parts by weight of nonylphenol polyglycol ether To produce a suitable preparation of active compound, three parts by weight of active compound were mixed with seven parts by weight of the solvent mixture indicated above, and the concentrate thus obtained was diluted with water to the desired concentration.

10 adult *Boophilus microplus* res. were immersed for 1 minute in the active compound preparation to be tested. After transfer to plastic beakers and storage in a climatically controlled chamber, the degree of destruction was determined.

In this test, for example, the following compounds showed a superior action compared with the prior art: (1) and (2).

EXAMPLE 10

Test with *Psoroptes cuniculi*

Solvent:
35 parts by weight of ethylene glycol monomethyl ether
35 parts by weight of nonylphenol polyglycol ether To produce a suitable preparation of active compound, three parts by weight of active compound were mixed with seven parts by weight of the solvent mixture indicated above, and the concentrate thus obtained was diluted with water to the desired concentration.

About 10–25 *Psoroptes cuniculi* were introduced into 1 ml of the active compound preparation to be tested, which had been pipetted into tablet nests of a deep-drawn pack. After 24 hours, the degree of destruction was determined.

In this test, for example, the following compound showed a superior action compared with the prior art: (1).

EXAMPLE

Test with *Stomoxys calcitrans*

Solvent:
35 parts by weight of ethylene glycol monomethyl ether
35 parts by weight of nonylphenol polyglycol ether To produce a suitable preparation of active compound, three parts by weight of active compound were mixed with seven parts by weight of the solvent mixture indicated above, and the concentrate thus obtained was diluted with water to the desired concentration.

10 adult *Stomoxys calcitrans* were placed in Petri dishes containing filter paper discs of appropriate size which had been saturated one day before the start of the experiment with 1 ml of the active compound preparation to be tested. After 3 hours, the degree of destruction was determined.

In this test, for example, the following compound showed a superior action compared with the prior art: (1).

It will be appreciated that the instant specification and examples are set forth by way of illustration and not limitation, and that various modifications and changes may be made without departing from the spirit and scope of the present invention.

What is claimed is:

1. A fluorine-substituted spirocarboxylic acid benzyl ester of the formula

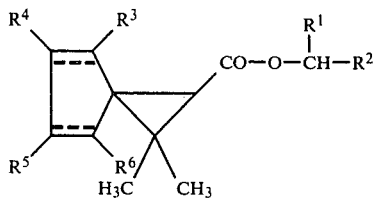

in which
R¹ represents hydrogen, cyano or alkyl, alkenyl or alkynyl, with in each case up to 4 carbon atoms,
R² represents a phenyl radical which is substituted by halogen and/or by optionally halogen-substituted phenoxy, with the proviso that the radical R² contains in total at least one fluorine substituent, and
R³, R⁴, R⁵ and R⁶ each represent hydrogen, halogen or alkyl, or
R³ and R⁴, taken together, and/or R⁵ and R⁶, taken together, represent alkanediyl (alkylene) or a fused-on benzo radical,
and the C atoms of the 5-member spirocyclic ring are linked to one another either by double bonds or by single bonds.

2. A compound according to claim 1, in which
R¹ represents hydrogen or cyano,
R² represents pentafluorophenyl, 4-fluoro-3-phenoxyphenyl, 3(4-fluoro-phenoxy)-phenyl or 4-fluoro-3-(4-fluoro-phenoxy)-phenyl,
R³ and R⁴ represent hydrogen and
R⁵ and R⁶ together represent a fused-on benzo radical,
and at the same time the carbon atoms bonded to R³ and R⁴ and to R⁵ and R⁶ are linked to one another via double bonds.

3. A compound according to claim 1, wherein such compound is 3,3-dimethylspiro-(cyclopropane-1,1'-indene)2-carboxylic acid α-cyano-3-phenoxy-4-fluoro-benzyl ester of the formula

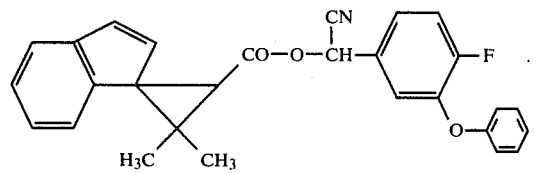

4. A compound according to claim 1, wherein such compound is 3,3-dimethylspiro-(cyclopropane-1,1'-indene)-2-carboxylic acid 3-phenoxy-4-fluoro-benzyl ester of the formula

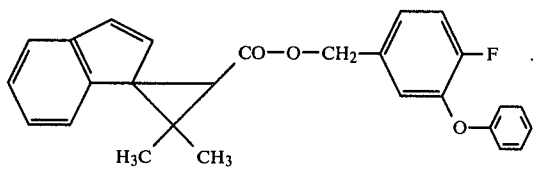

5. An arthropodicidal composition, comprising an anthropodicidally effective amount of a compound according to claim 1 in admixture with a diluent.

6. A method of combating arthropods which comprises applying to the arthropods, or to a habitat thereof, an anthropodicidally effective amount of a compound according to claim 1.

7. A method of combating arthropods which comprises applying to the arthropods, or to a habitat thereof, an anthropodicidally effective amount of a compound according to claim 6, wherein such compound is 3,3-dimethylspiro(cyclopropane-1,1'-indene)-2-carboxylic acid α-cyano-3-phenoxy-4-fluoro-benzyl ester.

8. A method of combating arthropods which comprises applying to the arthropods, or to a habitat thereof, an anthropodicidally effective amount of a compound according to claim 6, wherein such compound is 3,3-dimethylspiro(cyclopropane-1,1'-indene)-2-carboxylic acid 3-phenoxy-4-fluoro-benzyl ester.

* * * * *